United States Patent [19]
Henderson

[11] Patent Number: 5,376,071
[45] Date of Patent: Dec. 27, 1994

[54] INTRAVENOUS CATHETER ASSEMBLY AND METHOD OF INSERTION

[76] Inventor: David D. Henderson, 365 Laurel St., Hartford, Conn. 06106

[21] Appl. No.: 155,077

[22] Filed: Nov. 19, 1993

[51] Int. Cl.$^5$ ............................................. A61M 5/00
[52] U.S. Cl. .................... 604/53; 604/169; 604/246
[58] Field of Search ............. 604/83, 82, 167, 168, 604/248, 246, 164, 317, 322, 169, 53

[56] References Cited

U.S. PATENT DOCUMENTS

| | | | |
|---|---|---|---|
| 2,261,213 | 11/1941 | Bierman | 604/248 |
| 3,276,472 | 10/1966 | Jinkens et al. | 604/83 X |
| 3,313,299 | 4/1967 | Spademan . | |
| 3,434,691 | 3/1969 | Hamilton | 604/248 X |
| 3,459,183 | 8/1969 | Ring et al. . | |
| 3,459,184 | 8/1969 | Ring . | |
| 3,774,604 | 11/1973 | Danielsson . | |
| 3,934,576 | 1/1976 | Danielsson . | |
| 3,977,400 | 8/1976 | Moorehead . | |
| 4,219,021 | 8/1980 | Fink . | |
| 4,312,343 | 1/1982 | LeVeen et al. | 604/211 |
| 4,447,235 | 5/1984 | Clarke . | |
| 4,496,348 | 1/1985 | Genese et al. . | |
| 4,540,411 | 9/1985 | Bodicky . | |
| 4,566,480 | 1/1986 | Parham . | |
| 4,865,583 | 9/1989 | Tu . | |
| 5,078,688 | 1/1992 | Lobodinzki et al. . | |
| 5,084,034 | 1/1992 | Zanotti . | |
| 5,199,947 | 4/1993 | Lopez et al. . | |

*Primary Examiner*—John D. Yasko
*Attorney, Agent, or Firm*—Deborah Schavey Ruff

[57] ABSTRACT

In general, the invention relates to an improved assembly for insertion of an intravenous catheter and method of insertion which minimizes or eliminates the potential for exposure to blood and other bodily fluids during the use and insertion of an intravenous catheter. An intravenous catheter hub has a side opening directly to connected to a port of a multi-port stopcock. A modified syringe and hollow-bore needle are attached directly to the base of the catheter and when properly inserted, the needle extends slightly beyond the tip of the catheter. After the needle is inserted beneath a patient's skin, the syringe is used to generate slight negative pressure so that blood immediately flows into the syringe as soon as a vein is punctured by the needle. The syringe is then removed and the flow of fluids into the patient may be regulated by the multi-port stopcock.

14 Claims, 2 Drawing Sheets

INTRAVENOUS CATHETER ASSEMBLY AND METHOD OF INSERTION

BACKGROUND OF THE INVENTION

1. Field of the Invention

This invention relates generally to the field of medical devices for delivering fluid and medication to patients and more particularly, this invention relates to improved intravenous catheters and a method of insertion which minimizes or eliminates the potential for exposure to blood and other bodily fluids during the use and insertion of these devices.

2. Description of the Related Art

In recent years the medical community has greatly increased emphasis on new and modified procedures which minimize or eliminate the potential risk of exposing health care workers to blood and other bodily fluids during medical procedures. This increased emphasis on safety is primarily the result of the AIDS epidemic. The AIDS epidemic has focused the attention of the medical community on virtually any potential risk for exposure to blood or other bodily fluids due to the potentially devastating consequences of such exposure. Many of the advances arising out of these concerns have solved problems relating to the risk of puncture wounds from exposed needles which are used for injecting medications and inserting catheters.

Although there have been many improvements in this area, none have presented a practical solution to the problems associated with the use and initial insertion of intravenous catheters. This is true despite the fact that the insertion of intravenous catheters is one of the most commonly performed procedures in hospitals today and the manner in which it is performed is far from safe. The greatest danger posed by this procedure is the risk of contracting HIV from exposure to blood. There are other additional risks associated with exposure to blood and other bodily fluids during the insertion of intravenous catheters such as the risk of contracting vital hepatitis. These risks could also be reduced or eliminated through the use of an improved catheter assembly and modified procedure for inserting intravenous catheters.

Intravenous catheters are well known in the art and are widely used to deliver intravenous fluids and medications to patients every day. There are new catheters for long term central intravenous access and a myriad of attachments to augment the utility of a given intravenous site. However, the basic intravenous catheter and the method of insertion have remained unchanged for decades.

Conventional basic intravenous access involves the use of a flexible radiopaque catheter which is inserted in conjunction with a hollow bore needle. The catheter is generally constructed of a thin wall tube of flexible material, which is typically polytetrafluorothene sold under the trademark (TEFLON) or polyethylene. This material is connected to a connection bracket or base. The hollow bore needle is of a slightly smaller gauge and slightly longer than the catheter so that it may be easily introduced through the catheter while also remaining in sealing engagement with the catheter. When the needle is properly situated for insertion, the tip of the needle extends slightly beyond the tip of the catheter. A health care worker will insert the needle and catheter in this relationship through the skin of a patient and into a vein. When a vein is punctured in this manner, blood flows through the needle and out the needle hub which generally remains open. The needle is then pulled back slightly from the tip of the catheter and the catheter is then advanced further into the vein. Once the catheter is fully inserted, the needle is completely withdrawn and intravenous tubing is attached to the open hub of the catheter. This method, even in the most adept and experienced hands exposes the health care worker to the blood of the patient when the needle and catheter are initially inserted into the vein and when intravenous tubing is attached to the catheter.

Another problem associated with the insertion of a conventional intravenous catheter is that the health care worker is typically unaware of when the needle has initially punctured the patient's vein during insertion because there is a delay between the time when the needle initially punctures the vein and the point in time at which blood flows back through the catheter. This in many instances causes the health care worker to transect the vein or puncture the vein in numerous locations while attempting to locate the vein and insert the catheter. This occurs especially when the procedure is performed by inexperienced individuals or when a patient has poor circulation.

Others have suggested modified designs and procedures as potential solutions to the problems associated with intravenous catheters. However, none have gained acceptance as a practical solution to these problems. One such design can be found in U.S. Pat. No. 3,774,604 invented by Danielsson. This patent describes an infusion cannula assembly which employs a catheter directly connected to one port of a multi-position valve or stopcock. In this design, a needle is inserted into a port of the multi-position valve located directly opposite the port connected to the catheter. The needle is inserted through the multi-position valve and into the catheter. The catheter is then inserted in the same way as the conventional catheters previously discussed. The advantage that this design provides is that the multi-position valve may be closed to prevent blood from escaping through the base of the catheter once the catheter has been fully inserted. One problem with this solution is that needles used with this design must be significantly longer than needles designed for the insertion of conventional catheters. These longer needles are much more susceptible to breaking and also present a greater risk of accidentally sticking a health care worker or patient. This design is also very awkward to use in that a person using this device must close the valve while removing the needle to prevent blood from escaping from the port of the stopcock opposite the catheter. Additionally, the insertion of the needle through the multi-position valve creates the risk of shearing the needle in the valve.

Another solution to these problems can be found in U.S. Pat. No. 3,459,183 issued to Ring et al. This reference describes a catheter placement unit which incorporates an anesthetic in a resilient container attached to the needle. The needle is inserted into the catheter and the catheter and needle are then inserted beneath the skin of the patient. Once the needle and catheter are beneath the skin of the patient and prior to insertion into a vein, the resilient container is squeezed to inject the anesthetic beneath the skin of the patient. This also creates a slight negative pressure in the resilient container. When the needle and catheter are inserted into a vein, the slight negative pressure immediately causes blood flow back through the container which provides an indication of when the needle and catheter are inserted into the vein. Although this device prevents blood from escaping from the catheter once it has been inserted, there are several problems with this design. Most significantly, a longer needle is required due to the size of the catheter base. As noted, these longer needles are more susceptible to breakage and also increase the risk of puncture wounds. Additionally, this design has limited versatility because only a single fluid line can be connected to the patient.

Health care workers face the risks and problems associated with the use and insertion of intravenous catheters on a daily basis. There is a need in the medical field to minimize or eliminate the risk of exposure to blood or bodily fluids associated with the use and insertion of intravenous catheters. Additionally, there is a need to provide health care workers with an easily identifiable indication of when a vein is initially punctured during insertion of a catheter.

Accordingly, it is an object of the present invention to provide an improved intravenous catheter and method of insertion which minimizes or eliminates the risk of exposing health care workers to the blood and other bodily fluids of patients.

It is another object of the present invention to provide an improved intravenous catheter and method of insertion which provides health care workers with an indication of when a catheter is properly inserted within a vein.

It is a further object of the present invention to provide an improved intravenous catheter and method of insertion which minimizes or eliminates the risk of exposing health care workers to blood which can also be manufactured in an affordable disposable design.

Other objects and advantages of the present invention will become apparent from the following summary, drawings, and detailed description of the invention and its preferred embodiment.

SUMMARY OF THE INVENTION

The invention consists of a flexible radiopaque catheter which is attached to a plastic hub or base. The interior diameter of the hub progressively narrows along its length with an opening at the end adjacent to the catheter which is approximately the same size as the catheter. The hub includes another opening located at its side which directly communicates with the lumen of the catheter base. The side opening is designed for direct connection with the base of a multi-position valve or stopcock. In this design, the base of the stopcock has a passage which connects the side opening of the catheter to the well of the stopcock. The catheter is capable of fluid communication with any or all of the stopcock ports. In another design, the catheter hub has a side opening which has a luer or threaded fitting. The direct connection to the multi-position valve is made between the luer fitting of the catheter and the threaded fitting on a port of a multi-position valve.

The catheter hub or base also has an opening opposite the catheter which incorporates a latex sealing member inserted into this opening. The sealing member includes a depressed interior portion which forms a shallow well. The sealing member is situated such that the base of the sealing member is located adjacent to the side opening of the catheter base. The bottom of the well formed by the latex sealing member provides a target for a health care worker when inserting the needle and the sloping walls of the hub aid in guiding the needle into the catheter. This reduces the risk of improper insertion which might result in shearing of the teflon catheter. The latex sealing member seals the catheter during and after insertion of the needle and catheter to prevent blood from escaping out of the base of the catheter. The location of the latex sealing member with respect to the side opening of the catheter hub also prevents the possibility of an air embolism because there is no space proximal to the location where fluid enters the catheter where air could be trapped and later enter the patient's circulatory system. The latex sealing member could be similar in design to that disclosed in U.S. Pat. No. 3,853,127 invented by Spademan.

A hollow bore needle and modified syringe apparatus is designed to mate with the well formed by the latex sealing member in the base of the catheter hub. The syringe includes an interior threaded portion adjacent to the needle opening. The syringe plunger is designed to engage the threaded portion of the syringe so that the plunger may be advanced or retracted through rotation of the plunger when the plunger is located within the threaded portion. The plunger includes an arm which moves the plunger through the syringe in the same manner as a conventional syringe when the plunger is not engaged with the threaded portion of the syringe. The arm also has a lever extending from the end opposite the plunger which assists in rotation of the plunger.

Before inserting the needle into the catheter, the stopcock is opened to a port connected to an intravenous fluid line so that the catheter and stopcock may be flushed with fluid prior to insertion of the needle. The stopcock may then be closed or the source of fluid may otherwise be turned off. The needle is initially introduced through the base of the catheter and into the lumen of the catheter. The needle is then inserted to its fully forward position. As with conventional catheters, when fully inserted, the tip of the needle extends slightly beyond the tip of the catheter so that the bevel of the needle is exposed. The syringe may also include an optional exterior threaded fitting which is designed to engage another optional threaded fitting located at the opening in the base of the catheter. In this design, the needle may be secured by rotating its hub in a clockwise manner to engage a luer fitting located on the catheter hub. In the preferred embodiment, the syringe includes upper and lower protrusions which engage the catheter hub to prevent rotation of the syringe when the plunger is advanced and retracted through rotation. The catheter assembly is now ready for insertion.

First the blood vessel to be penetrated is selected and the overlaying skin is penetrated by the needle. When the tips of both the needle and catheter are beneath the skin, the lever at the end of the syringe plunger is rotated in a counterclockwise manner one quarter turn. This can easily be done using a third or fourth digit of the hand which holds the catheter. The rotation withdraws the plunger slightly creating a small amount of negative pressure. The needle and catheter are then inserted further under the skin and into the vein of the patient. As soon as the blood vessel is penetrated, there will be immediate blood flow back through the needle which is visible in the hub of the syringe. This is a result of the negative pressure in the syringe. After advancing the needle and catheter slightly further, the catheter is then advanced while the needle is held stationary. When the catheter is fully inserted, the needle is completely withdrawn from the catheter. Once the needle is completely withdrawn from the catheter, the valve of the stopcock may be adjusted to allow IV fluid to flow into the patient. The needle and syringe is then deposited in an appropriate medical waste container, and a cap may be placed on a threaded fitting at the opening of the catheter hub.

The invention may also incorporate other devices to produce alternate embodiments. These include the use of a self-adhesive strip which is attached to the base of the stopcock and catheter assembly to secure the assembly to the patient's skin. The stopcock and catheter hub may also be secured to a common base to aid in insertion of the catheter and add stability to the unit after insertion of the catheter. In an alternate design, a port of a multi-position valve may be attached directly to the side opening of the catheter. This connection may be made via a threaded fitting or the two devices may be molded into a single unit. It should be noted that the modified syringe is also capable of use with other conventional catheters and that the base is designed for compatibility with needles which are currently used for inserting intravenous catheters.

DETAILED DESCRIPTION OF THE INVENTION AND ITS PREFERRED EMBODIMENT

Figure 1:
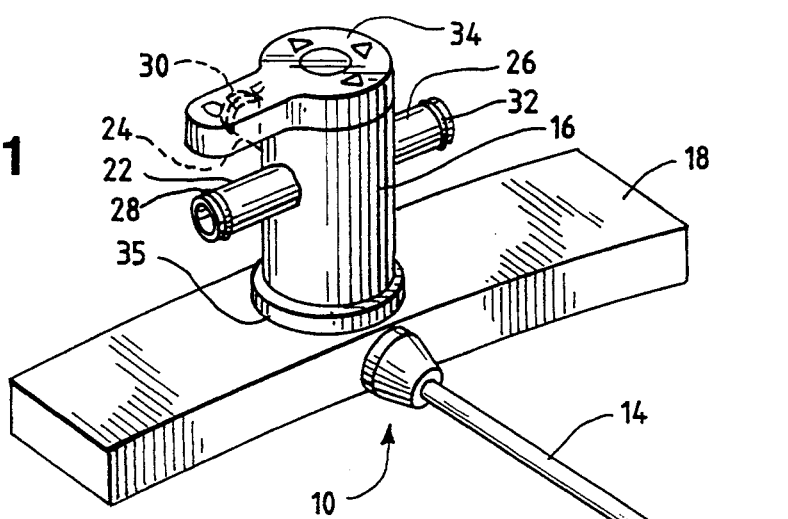
FIG. 1 is a drawing illustrating a catheter of the present invention which is directly connected to a base and multi-position valve.

Referring now to FIG. 1, the improved intravenous catheter of the present invention is shown generally at 10. The catheter assembly 10 includes a catheter 14 and a multi-position stopcock or valve 16. The catheter 14 and stopcock 16 are directly connected to a common base 18. The hollow base of the catheter is formed within the common base 18. The common base 18 supports the stopcock 16. Although in the preferred embodiment the common base is shown as having a wing shape, it will be appreciated that such a design is merely one of many possible choices. The base is designed to be compatible with needles which are currently used for inserting intravenous catheters and as such would not require an increase in needle length.

The stopcock 16 includes ports 22, 24, 26. Each port has a leur or threaded fitting indicated at 28, 30, 32. The stopcock also includes a valve control 34 that regulates which ports of the stopcock are in fluid communication with the well of the valve and catheter. The common base 18 also has a raised sealing member 35 which is used to form a seal between the stopcock 16 and the common base 18.

Figure 2:
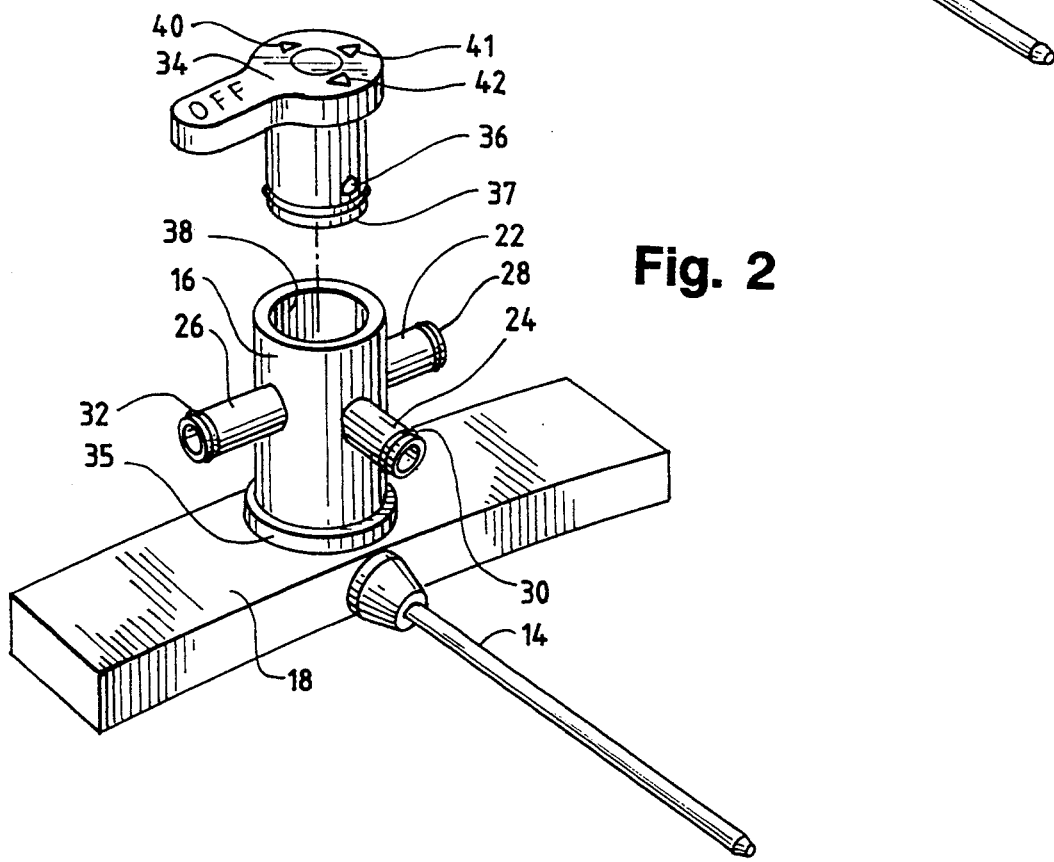
FIG. 2 illustrates the valve control of the stopcock when removed from the stopcock.

FIG. 2 is another view of the catheter and stopcock assembly which shows the valve control 34 removed from the stopcock 16. This view shows an access port 36 of the valve control 34. The access port 36 provides a fluid path from one of the stopcock ports 22, 24, 26 to the well of the stopcock 38. In this design there are three access ports located directly beneath each of the access port indicators 40, 41, 42 which are located on top of the valve control 34. A sealing rib 37 protrudes from the base of the valve control 34 to engage the interior well of the stopcock and form a seal therein. The sealing rib 37 may engage depressed ring located within the well of the stopcock to lock it in place and form a more secure seal. The depressed ring is not shown in this view.

The access port indicators 40, 41, 42 provide a user with the ability to select which of the ports 22, 24, 26 will be in fluid communication with the well of the stopcock 38. Whenever an access port indicator 40, 41, 42 is located above one of the ports 22, 24, 26 the port or ports will be in fluid communication with the well of the stopcock. The well of the stopcock may be sealed from the ports 22, 24, 26, when the access port indicators are located between adjacent ports. This view also shows the multi-position valve rotated 180 degrees from the view of FIG. 1. In the preferred embodiment, the multi-position valve is capable of rotation with respect to the base. This is a particularly useful advantage because medical stopcocks are generally bulky and awkward to use. However, it should be noted that rotation is not necessary.

Figure 3:
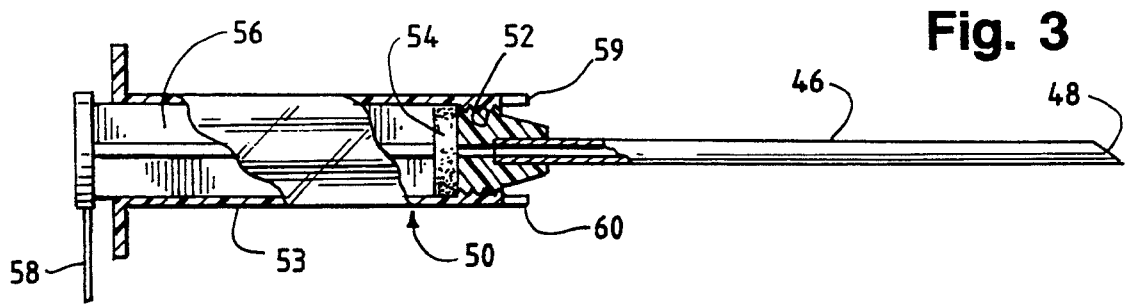
FIG. 3 illustrates the modified syringe apparatus.

FIG. 3 discloses the modified syringe of the present invention generally at 44. The modified syringe and needle assembly includes a hollow bore needle 46 which has a beveled tip 48. The hollow bore needle 46 is connected to a syringe 50 which includes an internally threaded portion 52 at the end of the syringe adjacent to the hollow bore needle 46 and a portion which is not threaded 53. The syringe also includes a plunger 54 and plunger arm 56. The plunger arm 56 is designed to advance and retract the plunger 54 through the non-threaded portion of the syringe 53. The plunger 54 is designed to engage the internally threaded portion of the syringe 52 such that clockwise rotation of the plunger advances the plunger and counterclockwise rotation retracts the plunger. The plunger arm 56 also includes a rotation lever 58 which assists in advancing and retracting the plunger through the internally threaded portion of the syringe. It will be appreciated that the internal threading of the syringe is a design choice and that the plunger arm could also engage a threaded member within the syringe to accomplish the same result. The syringe also includes upper and lower curved protrusions 59, 60 which are designed to engage the catheter hub to prevent rotation of the syringe when the plunger is advanced and retracted.

Figure 4:
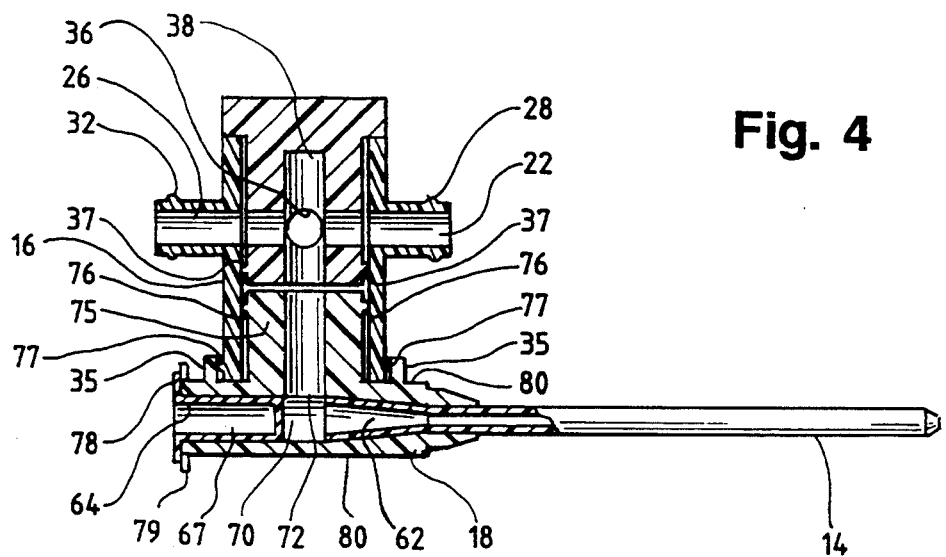
FIG. 4 illustrates a side view of the catheter and stopcock assembly.

FIG. 4 depicts a side view of the catheter and multi-position valve assembly. The catheter 14 is in fluid communication with the lumen of the catheter base 62 which is formed within the common base 18. The lumen of the catheter base 62 has an open end 64 which is opposite the catheter 14. The open end 64 is sealed by a latex sealing member 70 which is attached to the interior wall of the lumen of the catheter base 62. The latex sealing member 70 forms an open well 67 between the open end 64 of the catheter base and the base of the latex sealing member 70. The lumen of the catheter base has a second opening 72 which in the preferred embodiment is located adjacent to the base of the latex sealing member This second opening 72 is in direct fluid communication with the well of the stopcock 38.

FIG. 4 also shows the sealing rib 37 of the valve control 34 engaged with the interior wall of the multi-position valve 16. The interior wall of the stopcock 16 may also include a depressed ring for engaging the sealing rib 37 to provide a more secure seal and lock the valve control in place. The extension of the base 75 which forms the passage between the side opening 72 and the well of the stopcock 38 has an additional sealing rib 76 located on its upper exterior wall which also engages the interior wall of the stopcock. This sealing rib may also engage a depressed ring to form a better seal. The raised sealing member 35 which protrudes from the common base 18 incorporates a final depressed ring which is not shown for engaging a sealing rib 77 located on the exterior wall of the base of the stopcock.

Figure 5:
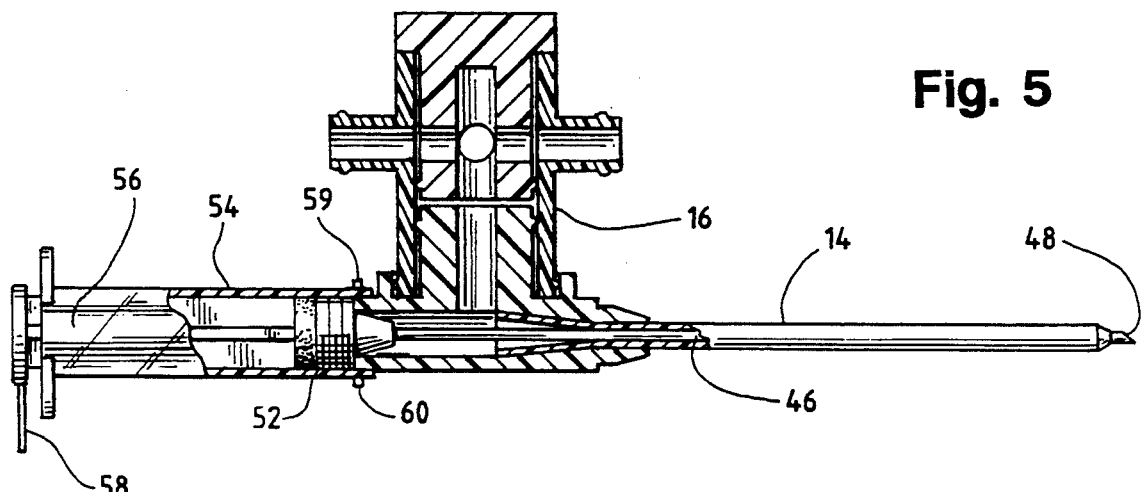
FIG. 5 illustrates a side view of the catheter and stopcock assembly with the syringe and needle fully inserted.

The interior wall 80 of the lumen of the catheter base 62 slopes inward so that portion of the lumen of the catheter base adjacent to the catheter 14 is approximately the same size as the catheter 14. Wing fittings 78, 79 are designed to mate with the respective upper and lower curved protrusions 59, 60 of the syringe. FIG. 5 depicts the modified syringe and needle when properly inserted into the catheter of the present invention. When ready for use the tip of the needle 48 extends slightly beyond the tip of the catheter 14. In this view, upper and lower curved protrusions of 59, 60 of the syringe have engaged the wing fittings 78, 79 of the catheter base.

Prior to inserting the needle into the catheter, the stopcock valve control is adjusted to open the stopcock to a port connected to an intravenous fluid line so that the catheter may be flushed with fluid prior to inserting the needle. The stopcock valve control 34 may then be adjusted to seal the well of the stopcock 38 or the source of the intravenous fluid may otherwise be turned off. The hollow bore needle 46 is then inserted through the base of the latex sealing member 70 at the open end 64 of the catheter base lumen 62 and into the catheter 14. The hollow bore needle 46 fits within the catheter 14 but remains in sealing engagement with the catheter 14. As noted, when fully inserted, the tip of the needle extends slightly beyond the tip of the catheter so that the needle tip or bevel 48 is exposed. The catheter is now ready for insertion.

Figure 6:
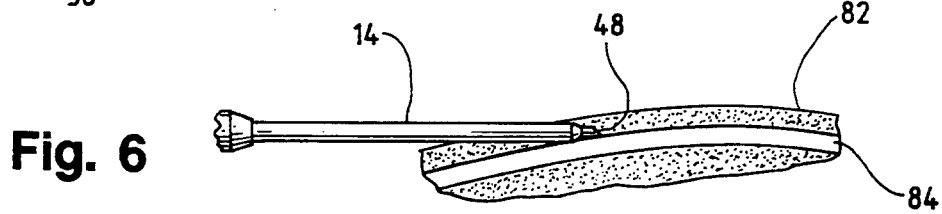
FIG. 6 illustrates the partial insertion of the catheter and needle of the present invention.
Figure 7:
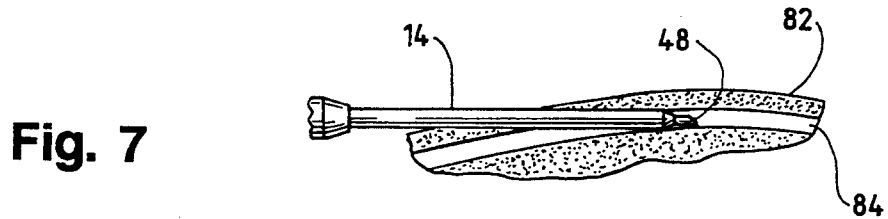
FIG. 7 illustrates the complete insertion of the catheter and needle of the present invention.
Figure 8:
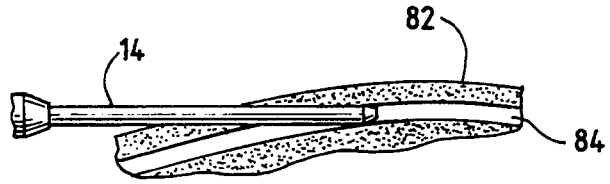
FIG. 8 illustrates the catheter of the present invention when properly inserted.

FIG. 6 shows the initial penetration of the skin 82 overlaying the blood vessel to be penetrated 84 by the tip of the needle 48 and catheter 14. When the tips of both the needle and catheter are beneath the skin, the rotation lever 58 at the end of the plunger arm 56 is rotated in a counterclockwise manner one quarter turn. This can easily be done using a third or fourth digit of the hand which holds the catheter. The rotation withdraws the plunger slightly creating a small amount of negative pressure. The needle and catheter are then inserted further under the skin 82 as indicated in FIG. 7 and into the vein of the patient 84. As soon as the blood vessel is penetrated, there will be immediate blood flow back through the needle which is visible in the hub of the syringe. After advancing the needle and catheter slightly further, the catheter is then advanced while the needle is held stationary. When the catheter is fully inserted, the needle is completely withdrawn from the catheter and its base. The catheter will then be located within the vein 84 as indicated in FIG. 8. Once the needle is completely withdrawn from the catheter 14 and hub 18, the valve of the stopcock may be adjusted to allow fluid to flow into the patient. A threaded cover may also be placed on the catheter hub opening 64 to provide a more secure seal over this opening. The threaded fitting is not shown. The needle and syringe may then deposited in an appropriate medical waste container or a blood sample may be used for analysis.

Although the invention has been disclosed in its preferred embodiment, it is contemplated that other designs may be selected which incorporate the disclosed invention. In particular, it is contemplated that the modified syringe of the present invention may be used with a conventional catheter. It is also contemplated that a catheter hub having a side opening may be directly connected to a port of a multi-position valve rather than through an opening in the base. In such a design, the side opening of the catheter base would have a leur or threaded fitting which would directly connect to the port of the stopcock. These designs may also incorporate an adhesive strip to secure the catheter assembly to the patient in order to prevent the catheter from dislodging.

While the invention has been particularly shown and described with reference to the preferred embodiment, it will be understood by those skilled in the art that variations in form, construction and arrangement may be made therein without departing from the scope and spirit of the invention. All such variations are intended to be covered by the appended claims.

What is claimed is:

1. An intravenous catheter assembly comprising a hollow base having a first end and a second end;
    a catheter connected to an opening at the first end;
    an opening at the second end;
    a syringe which mates with the opening at the second end;
    the syringe comprising a hollow body and a hollow bore needle which extends through the hollow base and catheter;
    a plunger located within the hollow body;
    a threaded member for advancing and retracting the plunger; a side opening in the hollow base, a multi-position valve having a plurality of ports, said valve directly connected to the side opening of the hollow base and moveable in said side opening to selectively provide fluid communication between said plurality of ports and said opening at the first end.

2. The intravenous catheter assembly of claim 1 further comprising a self-sealing latex member which seals the opening at the second end.

3. The intravenous catheter assembly of claim 1 further comprising a sealing cap engageable with said hollow base for sealing the opening at the second end.

4. The intravenous catheter assembly of claim 1 wherein the multi-position valve is directly connected to the side opening of the hollow base through a threaded fitting on said side opening.

5. The intravenous catheter assembly of claim 1 wherein said multi-position valve is moveable in said side opening to selectively provide fluid communication between at least one said plurality of ports and said opening at the first end.

6. The intravenous catheter of claim 1 wherein said multi-position valve is moveable in said side opening to selectively prevent fluid communication between said plurality ports and said opening at the first end.

7. The intravenous catheter of claim 1 wherein said multi-position valve is moveable in said side opening to provide fluid communication between at least two of said plurality ports and said opening at the first end.

8. An intravenous catheter assembly comprising a hollow base having a first end and a second end, said hollow base located within a wing-shaped supporting brace;

a catheter connected to an opening at the first end;

an opening at the second end;

a side opening in the hollow base;

a multi-position valve directly connected to the side opening in the hollow base, said multi-position valve having an open base which is directly connected to the side hollow base and which is in fluid connection with the well of the multi-position valve;

a syringe which mates with the opening at the second end;

the syringe comprising a hollow body and a hollow bore needle adapted to extend through the hollow base and catheter without interfering with the operation of said multi-position valve;

a plunger located within the hollow body;

a threaded member for advancing and retracting said plunger.

9. The intravenous catheter assembly of claim 8 further comprising a self-sealing latex member which seals the opening at the second end.

10. The intravenous catheter assembly of claim 8 further comprising a sealing cap engageable with said hollow base for sealing the opening at the second end.

11. An intravenous catheter assembly comprising a hollow catheter base;

a catheter directly connected to said hollow catheter base;

means for selectively regulating fluid flow from a plurality of fluid sources through the hollow catheter base and catheter; and a syringe including means for applying negative pressure to a needle connected to the syringe, said needle adapted to extend through a first opening in said catheter base and into said catheter and be removable from said catheter base and catheter without permitting escape of bodily fluid externally of said catheter assembly.

12. The catheter assembly of claim 11 wherein said means for selectively regulating fluid flow includes a multi-position valve seated in a second opening into said catheter base for selectively regulating fluid flow from said plurality of fluid sources through said catheter base and catheter.

13. The catheter assembly of claim 12 further including a plurality of fluid ports extending into said second opening.

14. The catheter assembly of claim 11 further comprising a self-sealing latex member for sealing said first opening.

* * * * *